United States Patent [19]

Caruso

[11] Patent Number: 4,978,661
[45] Date of Patent: Dec. 18, 1990

[54] USE OF 6-HALO-4-QUINOLONE COMPOUNDS AND PHARMACEUTICAL COMPOSITIONS THEREOF FOR THE PREPARATION OF A MEDICAMENT FOR THE THERAPEUTICAL APPLICATION IN RHEUMATOID ARTHRITIS

[76] Inventor: Innocenzo Caruso, Via Wittgens, 5, 20100 Milan, Italy

[21] Appl. No.: 392,475

[22] Filed: Aug. 11, 1989

[30] Foreign Application Priority Data

Sep. 29, 1988 [IT] Italy ............................... 22114 A/88
May 22, 1989 [IT] Italy ............................... 20585 A/89

[51] Int. Cl.$^5$ .......................................... A61K 31/495
[52] U.S. Cl. .............................. 514/224.5; 514/230.2; 514/254
[58] Field of Search ................... 514/224.5, 230.2, 254

[56] References Cited

U.S. PATENT DOCUMENTS 4,772,605  9/1988  Naik et al. .

OTHER PUBLICATIONS

Bayer et al., The Journal of Infectious Diseases, vol. 152, No. 4 (Oct. 1985), pp. 811–816.
Prere, et al., Chemical Abstracts, 105:75803j (1986).
The Merck Index, 11th ed., 1989, Merck and Co., Inc., Rahway, N.J. pp. 360, 1118.

*Primary Examiner*—Mukund J. Shah
*Assistant Examiner*—Philip Datlow
*Attorney, Agent, or Firm*—Oblon, Spivak, McClelland, Maier & Neustadt

[57] ABSTRACT

The present invention relates to the use of 6-halo-4-quinolone derivatives and pharmaceutical compositions comprising them as active ingredient, for the preparation of a medicament for the therapeutical application in rheumatoid arthritis.

Quinolone derivatives can be intra-articularly administered and act on different points of the pathological process of rheumathoid arthritis without local and general toxicity.

7 Claims, No Drawings

USE OF 6-HALO-4-QUINOLONE COMPOUNDS AND PHARMACEUTICAL COMPOSITIONS THEREOF FOR THE PREPARATION OF A MEDICAMENT FOR THE THERAPEUTICAL APPLICATION IN RHEUMATOID ARTHRITIS

The present invention relates to the use of 6-halo-4-quinolone compounds and to pharmaceutical compositions thereof for the preparation of a medicament useful in therapy of rheumatoid arthritis.

Rheumatoid arthritis (RA) is a primary illness of the articulations (synovitis) that may cause systemic complications, very often later in its clinical course. The pathologic process is characterized by an unceasable proliferation of the synovial tissue causing the formation of the so called "pannus" which yields the gradual destruction of the articulation by invading the cartilage and subchondral bone. It is generally accepted that a genetic predisposition may exist which causes an abnormal reactivity in these patients and/or a loss of the mechanisms of tissue control.

It has been hypothized that rheumatoid inflammatory process, started by a yet unknown etiologic agent, becomes self-perpetuating either for the unability of the patient to get rid of the exogenous antigen inducing it (retained antigen), or for an induced autoimmunization against a structure of the same organism (Ig G, Collagen proteins, etc.), such structure being degraded during an aspecific inflammation.

The traditional therapy of RA is based on the use of two kinds of pharmaceutical products:

(a) the anti-inflammatory agents, such as aspirin-like drugs or corticosteroids;

(b) slow-acting antirheumatic drugs (SARDS), such as for example: antimalarial agents, gold salts, penicillamine, cyclophosphamide, azathioprine, methotrexate and others.

Anti-inflammatory drugs have a pure symptomatic activity and do not change the natural hystory of the illness. They lower inflammation and pain and improve the articular motion. They are drugs acting quickly in RA, within 3–7 days from the administration, nevertheless clinical symptomatology reappears as soon as the treatment is stopped and the tissues are consequently deprived of the presence of the drugs.

Their side effects are more frequent and more severe in the stomach where they can cause gastric erosions, ulcerations and haemorrhages (Armstrong C. P., Blower A. l., Gut, 1987, 28, 527–532).

Although antiinflammatories have an important place in the therapy of RA improving the quality of life of treated patients, they are ineffective at all on the progression of anatomic lesions and in preventing or limiting the functional incapacity and disability.

The so-called SARDS are characterized by their very slow setting up of the effect (2–3 months). Their administration leads to a reduction of pain, rigidity and articular swelling in 60% of the cases. Nevertheless anatomic lesions go on inexorably even in cases in which clinic improvement proceeds with a normalization of acute phase proteins (ESR).

In the "Guidelines for the clinical investigation of drugs used in rheumatic diseases" (March 1985) the World Health Organisation (WHO) pointed out that the therapeutic activity of these drugs is not so effective to modify the long term outcome, and for this reason it is completely wrong to identify them as drugs which can modify the natural history of arthritis, as it was sometime said.

The SARDS are extremely toxic, probably the most toxic ones of the whole world pharmacopoeia, with side effects which are often irreversible even after interruption of the treatment.

The more frequently injured organs are marrow, stomach and liver, but the harmful effect can be even sistemic. As a matter of fact an increased mortality has been found in patients suffering from RA and treated with such a therapy.

In arthritic patients treated with immunodepressive agents such as azathioprine, an increased occurrence of neoplasias was also reported (Hazleman B., Am. J. Med., 1985, 78 (suppl. 1A), 39–43).

Rifamycin SV, an antibiotic used in the therapy of pulmonary tuberculosis, is active against rheumatoid process, but at the same time it is so extremely painful during the intraarticular infiltration that a certain number of patients do not want to carry on the treatment.

It has been now unexpectedly found that 6-halo-4-quinolone derivatives are therapeutically effective in the treatment of RA and they are devoid of local and general toxicity.

The above-mentioned derivatives are already known in scientific literature and they are described as antimicrobial agents useful in the treatment of urinary and respiratory infections (Wolfson J. S. Hooper D. C., Antimicrob. Ag. Chemother., 1985, 28 (a), 581–586, and Cecchetti et all., J. Med. Chem., 1987, 30, 465–473).

This invention relates to the use of compound of the class consisting of 6-halo-4-quinolone compounds of formula:

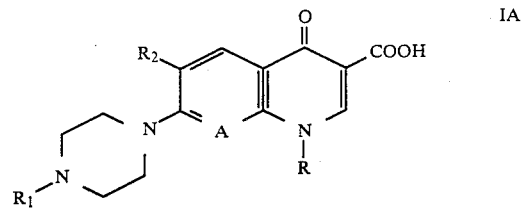

IA and

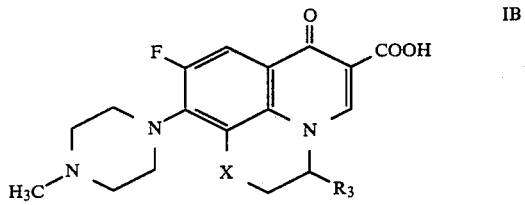

IB wherein R is selected from ethyl, cyclopropyl, a —NHCH$_3$ group and phenyl substituted in para position by a fluorine atom; R$_1$ is selected from hydrogen and lower alkyl with from 1 to 2 carbon atoms; R$_2$ represents a halogen atom; A represents a =CH— group or a nitrogen atom; X is selected from an oxygen and a sulfur atom; R$_3$ is methyl when X is an oxygen atom and it is hydrogen when X is a sulfur atom; and their pharmaceutically acceptable acid and base addition salts, for the preparation of the medicament for the therapeutic application in RA.

More particularly the present invention relates to the use of a compound of the formula:

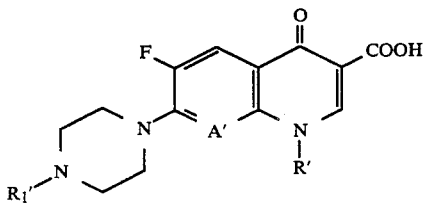

wherein R'₁ is selected from hydrogen and lower alkyl with from 1 to 2 carbon atoms; A' is selected from =CH— group and a nitrogen atom; R' is selected from ethyl and cyclopropyl; provided that when A' is a nitrogen atom, R'₁ is hydrogen and R' is ethyl, and when R' is cyclopropyl, A' is a =CH— group and R'₁ is hydrogen; and their pharmaceutically acceptable salts.

The term "pharmaceutically acceptable salts" means a salt obtained by the addition with a suitable organic or inorganic, non-toxic and pharmaceutically inert acid or base such as, for example, the hydrochloride, hydrobromide, acetate, propionate, butyrate, succinate, lactate, salts of addition with amino acids, etc.

It has been now surprisingly found that the above mentioned compounds, if intra-articularly administered, are therapeutically effective against RA. Such a result is unexpected inasmuch no activity of the compound of formulas IA and IB relating to immunoinflammatory process was previously reported. Furthermore, no therapeutical activity of the same compounds against RA was ever described.

Additionally, literature widely describes the capability of quinolone derivatives of easily penetrating into cartilages and bones (Newman M., Clinical Pharmacocinetics, 1988, 14, 96) wherein they can even concentrate. As in the rheumatoid hand the erosions take origin in the tendon insertions on the bone (Bucleland-Wright J. C. Ann. Rheum. Dis. 1984, 43, 160), the advantage of using the compound of formula IA and IB becomes apparent when they are intra-articularly administered, because they can act on two different points of the pathological process of RA, i.e. synovial membrane and tendo-capsular insertion on the bone.

Another aspect of the present invention relates to a pharmaceutical composition useful in the treatment of RA, comprising, as active ingredient, a compound of formulas IA and IB or a pharmaceutically acceptable salt thereof together with a suitable pharmaceutical carrier.

Employing the 6-halo-4-quinolone derivatives of formula IA and IB both single articulations of arthritic patients (partial multilocal scheme) or all peripheral articulations can be treated; in the latter case both the clearly inflamed articulations and the apparently unaffected ones are comprised (extensive multilocal scheme). The latter scheme is applied in the cases of RA at the onset while the partial scheme fits to advanced forms.

The schemes provide that each articulation gets injected once a week and the infiltrations are made during the first 5 days of the week. The whole weekly dosage ranges between 50 and 500 mg depending on the fact that some or all of the peripheral articulations are treated. The weekly treatment scheme has to be repeated 7-10 times, hence the total treatment period ranges from 50 to 70 days during which each articulation gets infiltered 7-10 times.

The "multilocal" intra-articular treatment with 6-halo-4-quinolone derivatives of this invention induce the clinical remission of the early rheumatoid illness and prevent the setting of articular limited movement; this condition is to be considered very similar to a really true recovery. In the hereinafter described cases almost all patients, having a negative radiology at baseline, do not show radiological lesions during the following period of observation up to three years, while it is known that most arthritic patients (75-90%) have radiological lesions in the first two years of the illness, even if they are treated with one or more traditional therapies (gold salts, antimalarians, etc.).

The treatment of each single articulation of patients with advanced RA is always followed by a clinic improvement, the entity of which is correlated with the radiological grade existing at the beginning of the treatment (Table 2).

No remarkable side effects due to the administration of the invention compounds was observed.

In the present application the term "weekly treatment" means a treatment carried out during the first five days of the week.

The following examples illustrate better the present invention, without limiting it.

EXAMPLE

MATERIALS AND METHODS

The patients selected for the study with compounds of formula IA and IB have been divided into two groups:

Group A: comprising 10 patients with early rheumatoid arthritis who, according to the American Rheumatism Association criteria, were classified as classic or defined forms. Patients with probable rheumathoid arthritis were not included;

Group B: comprising 10 patients affected by advanced rheumatoid arthritis, mostly with articular deformities and some functional incapacity. Moreover all patients had radiological lesions of variable degree.

The patients that in the last 6 months had gold salts or other antirheumatic drugs (slow-acting) and patients which had any important clinic condition, such as for example renal, hepatic, cardiac insufficiency and the like, were excluded from the clinical study.

The intra-articular infiltrations were made in the different articulations following the usual infiltrative technique and according to two schemes of treatment:

(1) Extensive multilocal treatment. All peripheral articulations (except the distal interphalangeas) were infiltrated in one week. In Table 1 the distribution of the articulations is reported in relation with the days of treatment. This scheme was applied to patients with early rheumathoid arthritis (Group A);

(2) Partial multilocal treatment with which only some peripheral articulations were infiltred. This scheme was applied to the advanced rheumathoid arthritis (Group B).

In the advanced forms the articulations choosen for the treatment were those with signs of active inflammation while those with fibrous or bony anchylosis were instead excluded. As it has been already underlined, the weekly treatment both with the extensive multilocal treatment and the partial one was repeated for 7-10 times. The dose of compounds of formulas IA and IB was calculated for each articulation considering the treated relative surface. Giving the value of 100 to the surface of knee, the following coefficients have been adapted for the other articulations: 0.90 for the hip; 0.250 for the shoulder, the elbow and the ankle; 0.125 for the wrist; 0.05 for small joints (metacarpophalangeas, proximal interphalangeas and metatarsophalangeas). If, for example, in the knee one dose of 100 mg/5 ml of 6-halo-4-quinolone derivative was injected, the maximal dose for the small articulations was 5 mg each one.

During the infiltrative treatment and in the following period of observation, patients were allowed to assume only a suitable dose of non-steroidal anti-inflammatory compounds. Moreover a program of rehabilitative exercises was set up in order to maintain the complete movement of each articulation.

The clinical and laboratory evaluations have been carried out at the beginning and at the end of the treatment. During the subsequent observation period, checks have been carried out every 3–6 months and the following subjective and objective parameters have been evaluated: duration of the morning stiffness, hand grip strenght, Ritchie articular index, pain severity evaluated by analogic scale (VAS), circumference of the proximal interphalangeal joints, number of swollen and painful articulations.

Furthermore at every check side effects were noted and the following laboratory tests were carried out: ESR, Latex test titer, ANA test titer, C Reactive protein, Haemoglobin, total and differential white blood cell count, platelet count, transaminases (AST, ALT), Y-GT, BUN, total bilirubin, creatinine, alkaline phosphatase, $C_3$ and $C_4$ complement fractions, urine analysis. In early rheumatoid arthritis patients (Group A), the radiographs of hands, wrists and feet have been carried out at the beginning of the study and every 6 months thereafter. The radiographic evaluation has been limited only to the remark of presence or absence of irreversible lesions. It has been commonly accepted that radiologic damage were irreversible when one of the following manifestations was present: narrowing of joint space of any degree, marked osteoporosis, multiple intraosseous erosions. The radiographs of each patient were read by a single observer unaware of the chronologic sequence and of the patient characteristics.

TABLE 1

Articulations distribution relating to the days of treatment. This scheme has been applied to the patients of Group A, i.e. the ones affected by early RA and without radiological lesion for whom definitive remission of the illness has been achieved.

| Day | Articulations | Administered Volumes (ml) | Administered Dosage* in each joint (mg) of Product A | Product B |
|---|---|---|---|---|
| Monday | Metacarpophalangeals (r) | 0.25–0.50 | 5 | 2.5 |
|  | Hip (r) | 3.00–5.00 | 90 | 45 |
|  | Knee (r) | 3.00–5.00 | 100 | 50 |
| Tuesday | Shoulder (r) | 1.00–2.50 | 25 | 12.5 |
|  | Wrist (l) | 0.50–1.00 | 12.5 | 6.25 |
|  | Proximal Interphalangeals (r) | 0.25–0.50 | 5 | 2.5 |
|  | Metacarpophalangeals (l) | 0.25–0.50 |  |  |
| Wednesday | Elbow (l) | 1.00–2.50 | 25 | 12.5 |
|  | Wrist (r) | 0.50–1.00 | 12.5 | 6.25 |
|  | Ankle (l) | 1.00–2.50 | 25 | 12.5 |
|  | Proximal Interphalangeals (l) | 0.25–0.50 | 5 | 2.5 |
| Thursday | Hip (l) | 3.00–5.00 | 90 | 45 |
|  | Knee (l) | 3.00–5.00 | 100 | 50 |
|  | Metatarsophalangeals (r) | 0.25–050 | 5 | 2.5 |
| Friday | Shoulder (l) | 1.00–2.50 | 25 | 12.5 |
|  | Elbow (r) | 1.00–2.50 | 25 | 12.5 |
|  | Ankle (l) | 1.00–2.50 | 25 | 12.5 |
|  | Metatarsophalangeals (l) | 0.25–0.50 | 5 | 2.5 |

*The reported dosages are in mg of 1-cyclopropyl-7-piperazinyl-6-fluoro-1,4-dihydro-3-carboxy-4-quinoline (Product B) and 1-ethyl-6-fluoro-7-(4-methyl-1-piperazinyl)-1,4-dihydro-3-carboxy-4-quinolone (Product A), the salts of which were used in the present clinical experiments.

Weekly doses of 250–500 mg of compounds of formula IA and IB have been administered to patients affected by early RA (Group A). Clinical remission and absence of radiological lesions in 90% of the cases were observed. One patient only did not respond to the treatment.

Table II sets forth the results of the present experiments which refer to patients affected by advanced RA.

TABLE II

Intraarticular treatment in advanced rheumatoid arthritis with derivatives of formula IA and IB in 10 patients.

| Treated Articulation (N.) | Clinical Result | | | | Relapses |
|---|---|---|---|---|---|
|  | I | II | III | IV |  |
| Knees (17) | ++++ | +++ | +++ | +++ | 2 |
| Hips (9) |  | +++ | +++ | +++ | 0 |
| Ankles (20) |  | ++++ | +++ | +++ | 1 |
| Hands (8) |  | ++ | ++ | ++ | 0 |
| Elbows (16) |  | ++ | +++ | +++ | 1 |
| Shoulders (10) |  | + | +++ | +++ | 0 |
| Total (80) |  |  |  |  | 1 |

I = Synovial effusion absorption,
II = Reduction of swelling,
III = Reduction of pain,
IV = Functional improvement.
Effect evaluation:
+ = minimum,
++ = fair,
+++ = good,
++++ = excellent.

I claim:

1. A method of treating rheumatoid arthritis, comprising administering to a patient in need thereof, a therapeutically effective amount of a compound of the formula

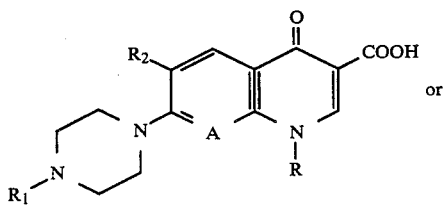

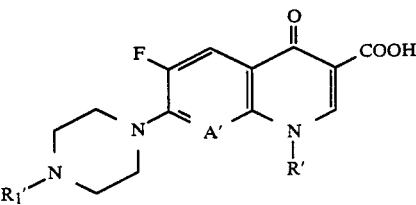

wherein $R'_1$ is hydrogen or $C_{1-2}$ lower alkyl, $A'$ is =CH— or a nitrogen atom, $R'$ is ethyl or cyclopropyl, provided that when $A'$ is nitrogen, $R'_1$ is hydrogen and $R'$ is ethyl, and when $R'$ is cyclopropyl, $A'$ is =CH— and $R'_1$ is hydrogen, and pharmaceutically acceptable salts thereof.

3. The method of claim 1, wherein said compound is 1-cyclopropyl-7-piperazinyl-6-fluoro-1,4-dihydro-3-carboxy-4-quinolone and pharmaceutically acceptable salts thereof.

4. The method of claim 1, wherein said compound is 1-ethyl-6-fluoro-7-(4-methyl-1-piperazinyl)-1,4-dihydro-3-carboxy-4-quinolone and pharmaceutically acceptable salts thereof.

5. The method of claim 3 or 4 wherein said compound is in unit dosage form comprising 50 mg to 500 mg of said compound.

6. The method of claim 1, comprising administering said compound and a pharmaceutically acceptable carrier therefor.

7. The method of claim 1, wherein said administering step comprises intra-articularly injecting said compound into said patient.

* * * * *

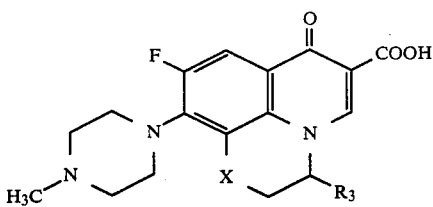

wherein R is ethyl, cyclopropyl, NHCH₃ or para-F-phenyl, $R_1$ is hydrogen or $C_{1-2}$ lower alkyl, $R_2$ is halogen, A is =CH— or a nitrogen atom, X is oxygen or sulfur, $R_3$ is methyl when X is oxygen and $R_3$ is hydrogen when X is sulfur, and pharmaceutically acceptable acid and base addition salts thereof.

2. The method of claim 1, wherein said compound has the formula